United States Patent [19]

Uemura et al.

[11] Patent Number: 5,308,769
[45] Date of Patent: May 3, 1994

[54] CANCER-RELATED HUMAN GALACTOSYLTRANSFERASE GT-II

[75] Inventors: Morito Uemura; Shinya Yoshida; Takao Uejima, all of Hino, Japan

[73] Assignee: Konica Corporation, Tokyo, Japan

[21] Appl. No.: 911,273

[22] Filed: Jul. 9, 1992

Related U.S. Application Data

[63] Continuation-in-part of Ser. No. 462,096, Jan. 8, 1990, abandoned, and Ser. No. 665,472, Mar. 6, 1991, abandoned.

[30] Foreign Application Priority Data

Jan. 11, 1989 [JP] Japan .................................. 1-4476
Mar. 6, 1990 [JP] Japan .................................. 2-54567

[51] Int. Cl.⁵ .................... C12N 9/10; A61K 39/00
[52] U.S. Cl. .................... 435/193; 435/815; 424/85.8
[58] Field of Search ............... 435/193, 81.5; 424/85.8

[56] References Cited

U.S. PATENT DOCUMENTS 4,205,129 1/1989 Podolsky et al. ............... 435/193
4,797,356 1/1989 Brandt et al. ..................... 435/7

FOREIGN PATENT DOCUMENTS 0226888 1/1987 European Pat. Off. .
0378188 7/1990 European Pat. Off. .

OTHER PUBLICATIONS

D. K. Podolsky et al, Biochem. and Biophys. Res. Commun., 65 (2) 545–551 (1975), "Galactosyltransfease Activities in Human Sera: Detection of a Cancer-Associated Isoenzyme".

Uemura et al, Cancer Research, 48, 5325–5334 (1988), "Characterization and Immunoassay of Human Tumor-Associated Galactosyltransferase Isoenzyme II" 65 (2) 545–551.

The Journal of Biological Chemistry, 254, 3983–3990 (1979).

S. Nozawa, "The Usefulness And Limitation of Sugar Antigen In Ovarian Cancers. With Special Reference To a New Tumor Marker, CA54/61," Chemical Abstracts, vol. 111, No. 11, 94720v (Sep. 11, 1989).

S. K. Chatterjee et al. "Murine Monoclonal Antibodies Against Galactosyl Transferase From The Ascites of Ovarian Cancer Patients," Chemical Abstracts, vol. 102, No. 1, 4295 x (Jan. 7, 1985).

M. Uemura et al, "Antiidiotypic Antibody to Galactosyl Transferase For Immunoassay And Cancer Diagnosis." Chemical Abstracts, vol. 110, No. 21, 191089h (May 22, 1989).

Primary Examiner—Douglas W. Robinson
Assistant Examiner—Jon P. Weber
Attorney, Agent, or Firm—Frishauf, Holtz, Goodman & Woodward

[57] ABSTRACT

A substantially purified cancer-related galactosyltransferase and a monoclonal antibody which may be used as a diagnostic reagent of cancer are disclosed. The galactosyltransferase of the present invention has a molecular weight of about 50,000 determined by SDS-polyacrylamide gel electrophoresis under reducing conditions and has a reactivity with MAb4880 under native conditions. A part of the galactosyltransferase self-associates and its reactivity with MAb4880 and the degree of self-association are promoted when it is reduced so that a part of which is detected in a fraction of a molecular weight of not less than 200,000 in gel permeation chromatography. The galactosyltransferase of the present invention can be used as a cancer marker or as a reagent for preparing a monoclonal antibody with a specificity to the galactosyltransferase, which monoclonal antibody can be used as a diagnostic of a cancer. The monoclonal antibody of the invention specifically reacts with the cancer-related galactosyltransferase of the invention.

5 Claims, 4 Drawing Sheets

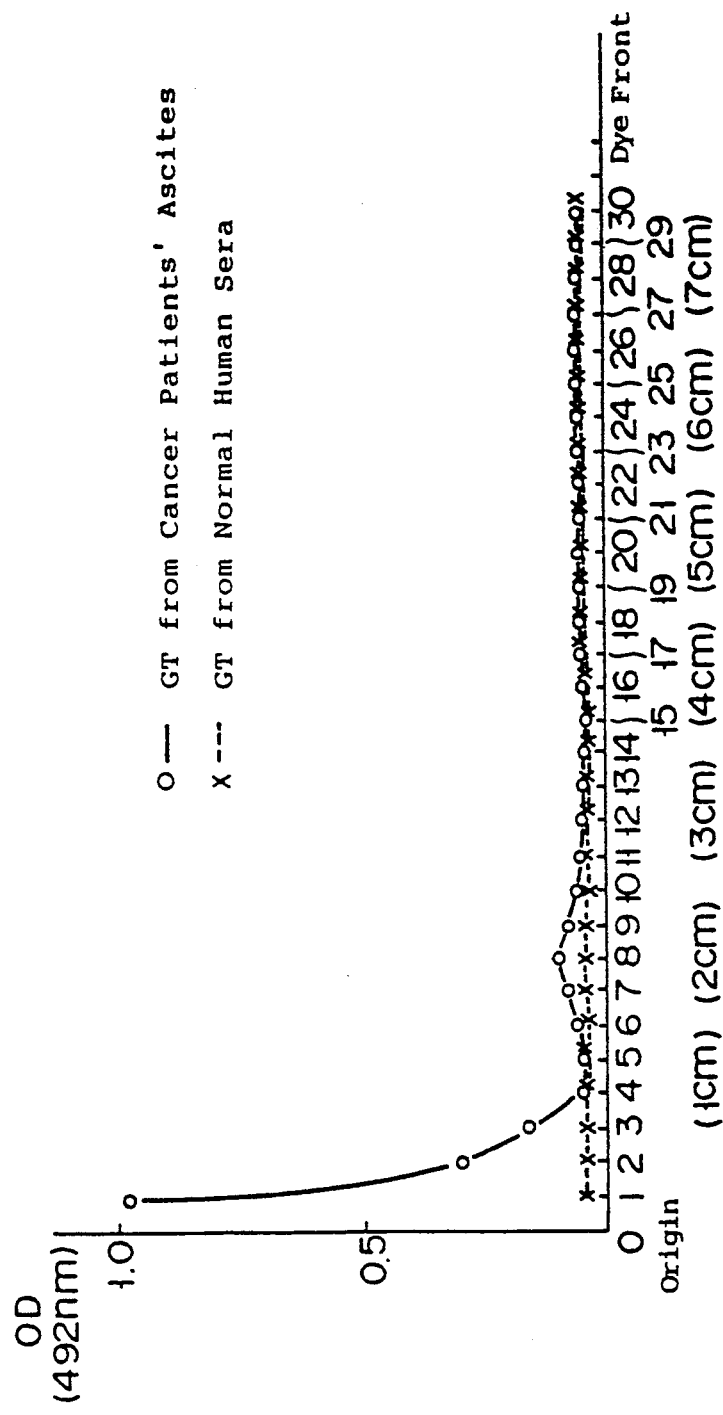
F I G. 1

CANCER-RELATED HUMAN GALACTOSYLTRANSFERASE GT-II

CROSS REFERENCE TO THE RELATED U.S. APPLICATIONS

This application is a continuation-in-part of United States patent application serial No. 07/462,096 filed on Jan. 8, 1990, now abandoned and of U.S. patent application Ser. No. 07/665,472 filed on Mar. 6, 1991, now abandoned.

BACKGROUND OF THE INVENTION

I. Field of the Invention

This invention relates to a novel cancer-related human galactosyltransferase. Since the cancer-related human galactosyltransferase of the present invention is mainly found in cancer patients, the galactosyltransferase of the present invention may be employed as a cancer marker. Thus, a monoclonal antibody specific to the galactosyltransferase of the present invention may be used as a diagnostic of cancer, and the galactosyltransferase of the present invention can be used as a reagent for preparing the monoclonal antibody.

Further, the present invention relates to a monoclonal antibody which is specific to a cancer-related human galactosyltransferase. The present invention also relates to a hybridoma producing the monoclonal antibody and to a method of measuring the cancer-related human galactosyltransferase using the monoclonal antibody of the present invention. The monoclonal antibody of the present invention may be used as a diagnostic reagent of cancer.

II. Description of the Related Art

Galactosyltransferase (hereinafter also referred to as "GT" for short) is an enzyme which catalyzes the transfer of galactose from uridine-5'-phosphogalactose (UDP-galactose) to non-reducing terminals of oligosaccharides of various glycoproteins or monosaccharides, which occurs in almost all the tissues in the body. Abnormal activity of GT has been recognized in various malignant tumors and the possibility of employing the GT as a cancer marker has been investigated. As a result, it was discovered that the level of GT-II which is an isozyme of GT in serum has close relationship with the existence of a cancer. The GT-II is defined as the GT enzyme activity in a band obtained in Native-PAGE (polyacrylamide gel electrophoresis), which has slower mobility than the GT-I which mainly exists in normal humans, as described in Biochem. Biophys. Res. Common, 65(2), pp.545–551, 1975. Further, MAb3872 which is a monoclonal antibody corresponding to the GT-II has been reported (Cancer Research, 48, pp.5325–5334, 1988). However, the nature of the GT-II has not yet been characterized.

SUMMARY OF THE INVENTION

Accordingly, the object of the present invention is to provide a novel galactosyltransferase which may be employed as a cancer marker and which can be assayed with high sensitivity.

The present inventors further studied the nature of the GT-II to find that a novel GT specific to cancer exists which is contained not only in the GT-II band, but also in the GT-I band and in the origin in the Native-PAGE. The cancer-related GT has the characteristics as mentioned below.

That is, the present invention provides a substantially purified cancer-related human galactosyltransferase which has a molecular weight of about 50,000 determined by SDS-polyacrylamide gel electrophoresis under reduced condition, which has a reactivity with MAb4880 under native conditions, a part of which self-associates, of which reactivity with MAb4880 (FERM BP-1758) and the degree of self-association are promoted when it is heated under reducing condition so that a part of which is detected in a fraction of a molecular weight of not less than 200,000 in gel permeation chromatography.

Since the cancer-related galactosyltransferase (hereinafter also referred to as CRGT) of the present invention mainly exists in the tissues of patients suffering from a cancer and it scarcely occurs in the tissues of normal humans, it can be employed as a cancer marker. Further, since the CRGT of the present invention can be employed as a cancer marker, a monoclonal antibody with a specificity to the CRGT of the present invention can be used as a diagnostic of a cancer. The CRGT of the present invention may also be used as a reagent for the preparation of the CRGT-specific monoclonal antibody.

Another object of the present invention is to provide a novel monoclonal antibody which specifically reacts with the cancer-related GT.

That is, the present invention further provides a monoclonal antibody which specifically reacts with a cancer-related human galactosyltransferase, said galactosyltransferase having a molecular weight of about 50,000 determined by SDS-polyacrylamide gel electrophoresis under reduced condition, said galactosyltransferase having a reactivity with MAb4880 (FERM BP-1758) under native conditions, a part of said galactosyltransferase self-associating, the reactivity of said galactosyltransferase with MAb4880 and the degree of self-association of said galactosyltransferase being promoted when said galactosyltransferase is heated under reducing conditions so that a part of said galactosyltransferase being detected in a fraction of a molecular weight of not less than 200,000 in gel permeation chromatography.

The present invention also provides a hybridoma which produces the monoclonal antibody of the present invention.

The present invention still further provides a method of measuring cancer-related human galactosyltransferase in a sample comprising specifically reacting the monoclonal antibody of the present invention with the cancer-related human galactosyltransferase possibly contained in said sample.

By the present invention, a novel monoclonal antibody which specifically recognizes the cancer-related human galactosyltransferase, as well as a hybridoma producing the monoclonal antibody and a method of measuring the cancer-related human galactosyltransferase using the monoclonal antibody was provided. By the present invention, the cancer-related human galactosyltransferase in a sample may be measured, so that the present invention contributes to the diagnosis of cancer such as ovarian cancer.

BRIEF DESCRIPTION OF THE DRAWINGS

FIG. 1 shows the results of MAb4880-sandwich assay for a solution into which a gel fraction of the band of the GT of the present invention or the normal human-originated GT was immersed, which band was obtained in Native-PAGE;

DETAILED DESCRIPTION OF THE PREFERRED EMBODIMENTS

Figure 2:
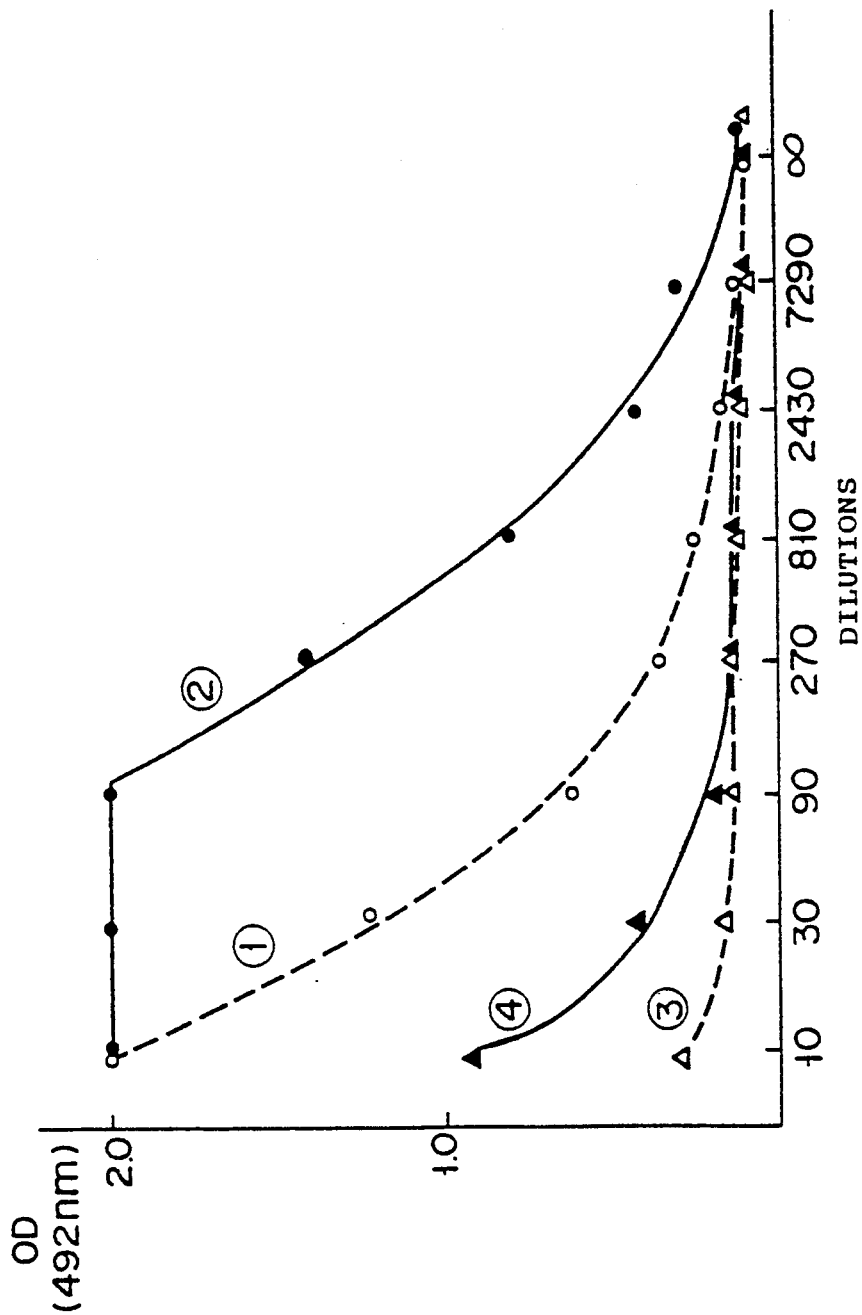
FIG. 2 shows the results of MAb4880-sandwich assay for a solution into which a gel fraction of the band of the non-treated GT of the present invention or the GT of the present invention after the treatment with 2-mercaptoethanol under heat was immersed, which band was obtained in Native-PAGE.

The CRGT of the present invention has a molecular weight of about 50,000 determined by SDS-PAGE under reducing condition after the treatment with 2-mercaptoethanol, as concretely described in the examples hereinbelow presented. This molecular weight of the CRGT of the present invention is identical with that of the normal human GT.

The CRGT of the present invention has a reactivity under the native conditions with MAb4880 which is a monoclonal antibody of which corresponding antigen is GT purified from ascites of a patient suffering from ovary cancer. The MAb4880 is prepared by the same manner as described in Cancer Research, vol. 48, p.5325, 1988, and disclosed in Japanese Laid Open Patent Application (Kokai) No. 174,100/87, which are herein incorporated by reference. A hybridoma producing the MAb4880 is deposited with Fermentation Research Institute in Japan in accordance with the Budapest Treaty under an accession number of BP-1758. The reactivity with the MAb4880 can be examined by the Western blotting method employing the MAb4880 as described in detail in the examples later described.

A part of the CRGT of the present invention self-associates in the native conditions. That is, two or more of the same protein molecules associate each other via an intramolecular interaction, so that associated molecules with a molecular weight larger than that of the non-associated single molecule by a factor of an integral number are detected. The binding between the protein molecules is not attained by a covalent bond and the associated molecules can be dissociated in certain conditions. This may be confirmed by the Western blotting as described in detail in the examples later described.

The reactivity of the CRGT of the present invention with the MAb4880 is promoted by a reduction treatment such as a treatment with 10 mM 2-mercaptoethanol. This may be confirmed by the SDS-PAGE after the reduction treatment or by the Western blotting method employing the MAb4880, which are described in detail in the examples later described.

The self-association of the CRGT of the present invention is enhanced by the above-described heat treatment under reducing condition so that the CRGT is detected in a fraction corresponding to a molecular weight of not less than 200,000 in a gel permeation chromatography, as detailed in the examples hereinbelow described.

The substrate and the function of the CRGT of the present invention are the same as those of the normal human GT. That is, the CRGT of the present invention catalyzes the reaction of the following equation:

$$UDP\text{-galactose} + Acceptor \rightarrow Galactose\text{-receptor} + UDP$$

(wherein the receptor is N-acetylglucosamine or an oligosaccharide, glycoprotein or a glycolipid having N-acetylglucosamine on a non-reducing terminals). Further, the optimal pH and the stable pH range of the CRGT are the same as those of the normal human GT, i.e., pH 6.0–8.0.

The CRGT of the present invention may be purified from ascites of a cancer patient, e.g., a patient suffering from ovary cancer, by α-lactoalbumin affinity chromatography in accordance with the method described in Cancer Research, vol. 48, p.5325, 1988 in the same manner as the normal human GT is purified, as described in detail in the examples hereinbelow described. It should be noted, however, the CRGT of the present invention exists not only in the patient suffering from ovary cancer but also in the patients suffering from other cancers such as bladder cancer, colorectal cancer, lung cancer, pancreas cancer, esophagus cancer and liver cancer. Further, the CRGT of the present invention occurs not only in ascites but also other body fluids such as serum.

As described above, the monoclonal antibody of the present invention specifically reacts with the above-described cancer-related GT. The MAb4880 employed in the definition of the cancer-related GT is a monoclonal antibody whose corresponding antigen is GT purified from ascites of a patient suffering from ovarian cancer. The MAb4880 is prepared by the same manner as described in Cancer Research, vol. 48, p.5325, 1988, and disclosed in Japanese Laid Open Patent Application (Kokai) No. 174,100/87. A hybridoma producing the MAb4880 is deposited with Fermentation Research Institute in Japan in accordance with the Budapest Treaty under an accession number of FERM BP-1758.

The monoclonal antibody of the present invention may be prepared by the so called hybridoma method using the cancer-related GT as the immunogen. The process of preparing the monoclonal antibody of the present invention will now be described in detail.

The immunogen used in the preparation of the monoclonal antibody of the present invention may be purified from ascites of a cancer patient, e.g., a patient suffering from ovarian cancer, by α-lactoalbumin affinity chromatography in accordance with the method described in Cancer Research, vol. 48, p.5325, 1988 in the same manner as the normal human GT is purified, as described in detail in the examples hereinbelow described. It should be noted, however, the cancer-related GT exists not only in the patients suffering from ovarian cancer but also in the patients suffering from other cancers such as bladder cancer, colorectal cancer, lung cancer, pancreas cancer, esophagus cancer and liver cancer. Further, the cancer-related GT occurs not only in ascites but also other body fluids such as serum.

A mammal such as mouse or rat is immunized with the immunogen. The immunization may be carried out by a conventional method. For example, the immunogen may be administered intraperitoneally or intravenously to an animal together with an adjuvant such as Freund's complete adjuvant.

Then antibody-producing cells such as spleen cells are collected from the immunized animal and the cells are fused with, for example, mouse myeloma cells. As the myeloma cells, various known myeloma cells such as X63-Ag 8.653 may be employed. As the fusing agent, polyethylene glycol may be employed. The mixing ratio of the antibody-producing cells to the myeloma cells may preferably be 1:1 to 10:1 in terms of the number of the cells.

After the cell fusion, by culturing the fused cells in a conventional selection medium such as HAT medium, hybridomas can be selected. Since the myeloma cells cannot be alive in HAT medium, the selection of the hybridomas can be attained by simply selecting the cells which grow in HAT medium.

After the colonies of the hybridomas sufficiently grew, the screening of the hybridoma producing the desired monoclonal antibody and the cloning of the hybridoma are carried out. The screening of the hybridoma may be carried out by a conventional method such as ELISA. The hybridomas producing a monoclonal antibody which reacts with the immunogen and which does not have cross-reactivity with serum proteins are selected and then cloned by the limiting dilution method. By this process, a desired cloned hybridoma producing the monoclonal antibody of the present invention may be obtained.

The monoclonal antibody of the present invention may be recovered by culturing the desired hybridoma in a culturing medium and separating the monoclonal antibody from the supernatant of the culture medium or by intraperitoneally administering the desired hybridoma to mice and recovering the monoclonal antibody from the ascites of the mice. Further, if desired, the monoclonal antibody of the present invention may be purified by conventional methods such as precipitation with ammonium sulfate, gel permeation chromatography and ion-exchange chromatography.

As will be concretely described in the examples below, by the above-described process, three monoclonal antibodies of the present invention, that is, monoclonal antibodies named MAb7907, MAb8513 and MAb8677 were obtained. These monoclonal antibodies have been deposited with Fermentation Research Institute of Japan under the Budapest Treaty, the accession numbers being given in the examples hereinbelow described.

The measurement of the cancer-related GT in a sample using the monoclonal antibody of the present invention may be accomplished according to a conventional immunoassay utilizing the specific antigen-antibody reaction. For example, the immunoassay may be carried out according to the sandwich assay which per se is well-known in the art. In the sandwich assay, the monoclonal antibody of the present invention may be fixed to an appropriate solid carrier such as microtiterplate or plastic beads and the fixed monoclonal antibody is made to contact the sample. Thereafter, a second antibody whose corresponding epitope is different from the that of the monoclonal antibody of the present invention, which second antibody is labelled with an appropriate marker such as a radioisotope (such as $^{125}I$) or peroxidase and then the solid carriers are washed, followed by measurement of the second antibody according to the marker attached thereto. In this case, as the second antibody, MAb4880 as well as monoclonal antibodies MAb8507 and MAb8628 may preferably be employed.

In cases where the monoclonal antibody of the present invention is used for diagnosis of cancer, body fluids, especially serum, may preferably be used as the sample.

It has been found that the monoclonal antibody of the present invention exhibits high specificity to the cancer-related GT in self-associated state, while most of the cancer-related GT molecules exist in the form of dissociated molecules with low molecular weight in serum. However, when the monoclonal antibody of the present invention is used in the fixed state, by carrying out the immunological reaction at a relatively high temperature, that is, preferably at 37°-56° C., the reactivity of the immobilized monoclonal antibody with the cancer-related GT may be promoted. This is presumably because that the three dimensional structure of the cancer-related GT is changed so that its reactivity with the monoclonal antibody is promoted.

The invention will now be described by way of examples thereof. It should be understood that the present invention is not limited to the examples below.

EXAMPLE 1

From 1 liter of ascites from a patient suffering from ovary cancer or from 2 liters of pooled normal human serum, GT was purified by α-lactoalbumin affinity chromatography in accordance with the description in Cancer Research, vol. 48, p.5325, 1988, to obtain 1.1 ml or 0.8 ml of GT, respectively. More particularly, the ascites or the serum was dialyzed overnight against purified water at 4° C. and the insoluble mass was removed by centrifugation. To the resulting solution, Tris-buffer (pH 7.2), manganese chloride (MnC12) and N-acetylglucosamine were added to attain the final level of 20 mM, 10 mM and 5 mM, respectively, and the resulting mixture was applied to an α-lactoalbumin affinity column (2.5 cm×50 cm). After the column was washed with 1 liter of the same buffer as mentioned above containing manganese chloride and N-glucosamine, elution was carried out with the same buffer but not containing N-acetylglucosamine to obtain GT fractions. The same chromatography operation as described above was repeated for the obtained GT fractions to further purify the GT. The resulting GT fractions were applied to an anti-human IgG agarose column (0.5×3 cm) in order to remove immunoglobulins, followed by being concentrated. The obtained GT originated from the cancer patient and the normal human had a protein level of 0.8 mg/ml and 0.5 mg/ml, respectively. Ten microliters each of the obtained GT originated from the cancer patient or the normal human was treated with dodecyl sodium sulfate (SDS) and 2-mercaptoethanol and the resultants were subjected to 4–20% SDS-PAGE on a slab gel sizing 10 cm ×10 cm (commercially available from Daiichi Kagaku Yakuhin, Co., Ltd.) under the following conditions, followed by silver staining:

| Buffer for Electrophoresis: | 25 mM Tris, 192 mM glycine, 0.1% SDS (pH 8.4) |
|---|---|
| Electric Current: | 60 mA consdtant current |
| Electrophoresis Time: | 1 hour |

As a result, both of the GT originated from the cancer patient and the GT originated from normal human exhibited a band corresponding to a molecular weight of 48,000-55,000, and other bands of impurities were not observed.

On the other hand, in place of the staining with silver, Western blotting was carried out in accordance with Proc. Natl. Acad. Sci. USA 76, 4350 (1979). In this Western blotting, the MAb4880 labelled with horse radish peroxidase (HRP) was used as the probe antibody. As a result, a band corresponding to the band obtained in the above-described silver-staining was observed, and the GT originated from the cancer patient was colored much more intensively than the GT originated from the normal human.

From these results, it was proved that the CRGT of the present invention can be purified by α-lactoalbumin affinity chromatography and that it has a molecular weight of about 50,000 determined by the SDS-PAGE under reducing condition as the normal human GT.

EXAMPLE 2

Ten microliters each of the GT from the cancer patient and the GT from the normal human which were purified in Example 1 was subjected to 4-15% Native-PAGE on a slab gel sizing 10 cm × 10 cm (commercially available from Daiichi Kagaku Yakuhin, Co., Ltd.) under the following conditions, followed by silver staining:

| | |
|---|---|
| Buffer for Electrophoresis: | 25 mM Tris, 192 mM glycine (pH 8.4) |
| Electric Current: | 30 mA constant current |
| Electrophoresis Time: | 2 hours |

As a result, as for the GT from the cancer patient, a broad band with an Rf value of 0.3-0.5 and a band tailing from the origin to the position of an Rf value of about 0.3 were obtained. On the other hand, as for the GT from the normal human, although the band corresponding to the Rf value of from about 0.3-0.5 was observed, the band tailing from the origin to the position of an Rf value of about 0.3 was observed only in the trace amount.

On the other hand, in place of the silver-staining, the gel (each sample lane) was cut into strips with a width of 0.25 cm, and each of the resulting strips was immersed in 100 ul of phosphate buffer (hereinafter referred to as PBS) containing 1% bovine serum albumin at 4° C. overnight. Fifty microliters of each of the immersion solutions was incubated with polystyrene beads coated with MAb4880 and 200 ul of PBS at 37° C. for 2 hours. The beads were then washed three times with PBS and MAb4880 labelled with horse radish peroxidase (hereinafter referred to as MAb4880-HRP) was added thereto. The mixture was allowed to react for 2 hours at room temperature. After the reaction, the beads were washed four times with PBS and o-phenylenediamine as a substrate was added to color the reaction mixture. The absorbance at 492 nm of the resulting reaction mixture was determined (MAb4880 sandwich assay). The results are shown in FIG. 1.

From these results, it was confirmed that a part of the CRGT of the present invention self-associates under the conditions of Native-PAGE to form associated molecules with a larger molecular weight.

EXAMPLE 3

The GT from the cancer patient or from the normal human purified in Example 1 was treated with 10 mM 2-mercaptoethanol at 80° C. for 3 minutes and was subjected to 4-15% Native-PAGE followed by silver-staining in the same manner as in Example 2. As for the GT from the cancer patient, the band tailing from the origin to the position of an Rf value of 0.3 almost disappeared and a band in the vicinity of the origin emerged in place thereof. The broad band of an Rf value of about 0.3-0.5 was observed as in Example 2, although the density of the silver-staining was somewhat reduced. As for the GT from the normal human, although a trace amount of a band in the vicinity of the origin was recognized, the results were not substantially changed from those in Example 2.

The gels obtained in Example 2 and the above-described gels after the heat treatment with 2-mercaptoethanol were subjected to the Western blotting as in Example 1 and were stained with MAb4880-HRP. Either of the gels obtained in Example 2 for the GT from the cancer patient or for the GT from the normal human exhibited substantially the same pattern as in the silver-staining in Example 2. In the blotting of the gels obtained in the Native-PAGE of the sample heat treated with 2-mercaptoethanol, only the band tailing from the origin was stained for the GT from the cancer patient. On the other hand, as to the GT from the normal human, only the origin was slightly stained.

From these results, it was confirmed that the self-association of the CRGT of the present invention is enhanced by the heat treatment with 2-mercaptoethanol so that its molecular weight is increased and the binding reactivity with the MAb4880 is prominently enhanced by the heat treatment with 2-mercaptoethanol and that the binding reactivity of the GT from normal human with the MAb4880 is reduced by the heat treatment with 2-mercaptoethanol.

EXAMPLE 4

The GT from the cancer patient or the GT from the normal human purified in Example 1 was treated with 10 mM 2-mercaptoethanol at 80° C. for 3 minutes. The GT was 10-fold to about 7000-fold diluted with 1% BSA-PBS and subjected to the sandwich assay using the MAb4880 as in Example 2. In another run, the GT was subjected to the sandwich assay without the heat treatment with 2-mercaptoethanol.

The results are shown in FIG. 2. In FIG. 2, curve 1 shows the results for the GT from the cancer patient without the treatment, curve 2 shows the results for the GT from the cancer patient which was subjected to the heat treatment with 2-mercaptoethanol, curve 3 shows the results for the GT from the normal human without the treatment and curve 4 shows the results for the GT from the normal human which was subjected to the heat treatment with 2-mercaptoethanol.

From these results, it was confirmed that the detection sensitivity in the MAb4880 sandwich assay of the CRGT of the present invention was drastically promoted by the 2-mercaptoethanol heat treatment, and that a large amount of the CRGT of the present invention exists in the ascites of cancer patients, although a small amount of it also exists in the serum of the normal humans.

EXAMPLE 5

Figure 3:
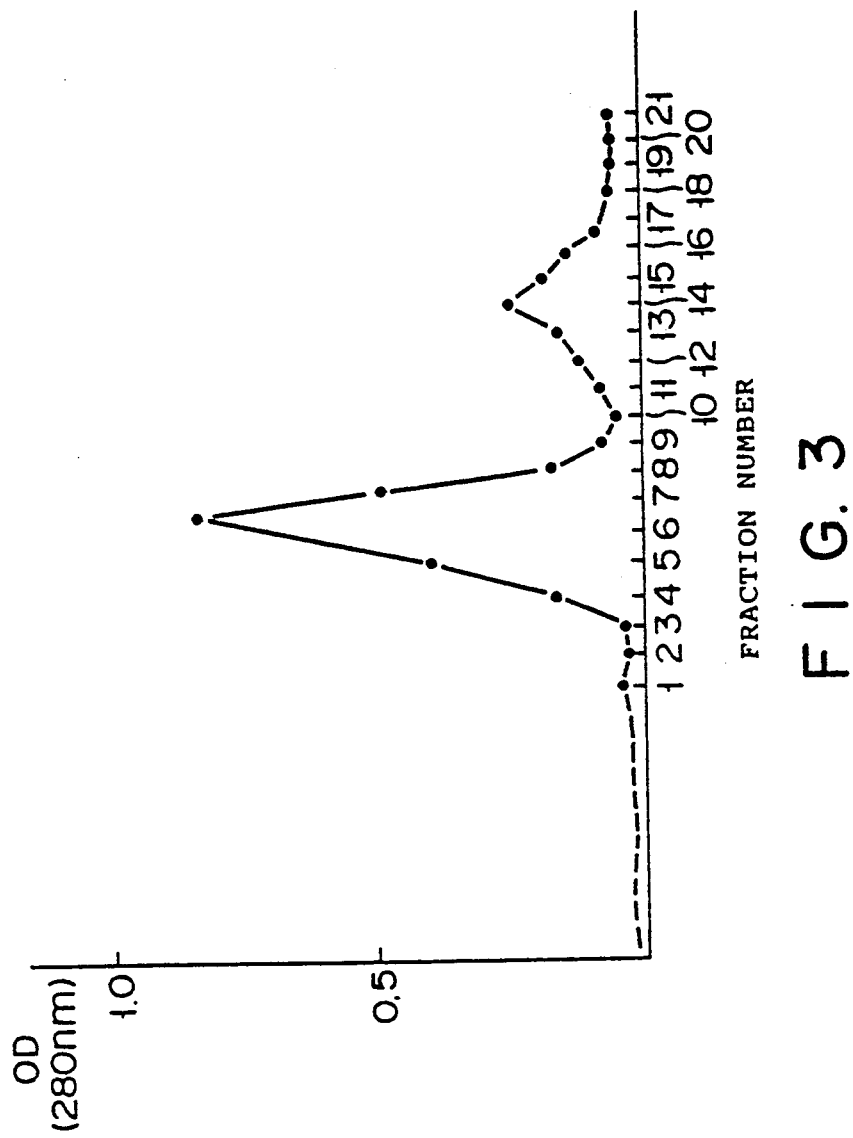
FIG. 3 is an elution curve obtained in a gel permeation chromatography of the GT of the present invention after the treatment with 2-mercaptoethanol under heat.

One hundred microliters aliquotes of each of the samples for the sandwich assay obtained in Example 4 were subjected to gel permeation chromatography on FPLC super rose-12 (commercially available from Pharmacia) using PBS as the solvent at a flow rate of 0.5 ml/min. The elution curve of the GT from the cancer patient heat treated with 2-mercaptoethanol is shown in FIG. 3. Two microliters aliquotes of the 20 fractions obtained from 10 minutes to 20 minutes from the commencement of the elution were directly blotted to nitrocellulose membranes and were reacted with MAb-4880 to color the same. The results are shown in Table 1. The intensity of the reaction is expressed by the following symbols.

++ : Strongly Colored
+ : Weakly Colored
± : Slightly Colored
— : Not Colored

As is apparent from Table 1, the self-association of the CRGT of the present invention is enhanced by the 2-mercaptoethanol treatment and so its molecular weight is increased so that it is detected in the fractions corresponding to a molecular weight of not less than 200,000 in the gel permeation chromatography.

TABLE 2-continued

| Beads Labelled Substance | MAb3872-HRP | MAb4880-HRP | MAb4880-HRP |
|---|---|---|---|
| Purified Product A | 0.082 | 0.904 | 1.890 |
| Purified Product B | 1.545 | 0.281 | 0.045 |

Purified Product A: GT purified by α-lactoalbumin affinity chromatography
Purified Product B: GT purified by MAb3872 affinity chromatography

EXAMPLE 7

Preparation of Immunogen

From 1 liter of ascites from a patient suffering from

TABLE 1

| | Molecular Weight Fraction No. | ∞ void 1 M. | | | | | | 500 T. | | | 200 T. | | | 100 T. | | | 50 T. | | | | |
|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 |
| GT from Cancer Patient | 2-ME and heat non-treated | — | — | — | — | ± | + | ± | — | — | — | — | — | — | — | ± | ± | — | — | — | — |
| | 2-ME and heat treated | — | — | — | ± | + | ++ | + | ± | — | — | — | — | — | — | — | — | — | — | — | — |
| GT from Normal Human | 2-ME and heat non-treated | — | — | — | — | — | — | — | — | — | — | — | — | — | — | — | ± | ± | — | — | • |
| | 2-ME and heat treated | — | — | — | — | — | ± | — | — | — | — | — | — | — | — | — | — | — | — | — | — |

2-ME: 2-mercaptoethanol
M.: Million
T.: Thousand

EXAMPLE 6

The monoclonal antibody MAb3872 (ATCC HB 8945) specific to the GT-II described in Cancer Research vol. 48, p.5325, 1988 was immobilized in an agarose gel activated with cyanogen bromide to prepare an affinity chromatography column (2.5 cm × 10 cm). About one liter of ascites of a patient suffering from ovary cancer was passed through the column at a flow rate of 50 ml/hr and the column was then washed with 500 ml of phosphate buffer (pH 7.3) containing 0.5 M NaCl. Then the elution was carried out with a glycine buffer (pH 2.8) containing 0.5M NaCl and the fractions exhibiting the reactivity with MAb3872 were pooled, followed by being concentrated to a volume of about 1 ml.

The sample purified by the MAb3872 affinity chromatography and the sample purified by the affinity chromatography in Example 1 were subjected to the assay mentioned below. The MAb4880-immobilized beads and the MAb4880-HRP were those prepared in Example 1. The MAb3872-immobilized beads and the MAb3872-HRP labelled substance were prepared in the same manner as in the case of MAb4880. The sample purified by the α-lactoalbumin was 500-fold diluted with 1% BSA-PBS and the sample purified by MAb-3872 affinity column was 100-fold diluted with the same buffer. The sandwich assay was conducted as in Example 2 for the combination of the immobilized beads and the labelled substance shown in Table 2. The determined absorbance is shown in Table 2.

As is apparent from Table 2, the CRGT of the present invention is different from GT-II with a reactivity with MAb3872, although some of the characteristics are common.

TABLE 2

| Immobilized | MAb3872 | MAb3872 | MAb4880 | ovarian cancer, GT was purified by α-lactoalbumin affinity chromatography in accordance with the description in Cancer Research, vol. 48, p.5325, 1988. More particularly, the ascites was dialyzed overnight against purified water at 4° C. and the insoluble mass was removed by centrifugation. To the resulting solution, Tris-buffer (pH 7.2), manganese chloride (MnCl2) and N-acetylglucosamine were added to attain the final level of 20 mM, 10 mM and 5 mM, respectively, and the resulting mixture was applied to an α-lactoalbumin affinity column (2.5 cm × 50 cm). After the column was washed with 1 liter of the same buffer as mentioned above containing manganese chloride and N-glucosamine, elution was carried out with the same buffer but not containing N-acetylglucosamine to obtain GT fractions. The same chromatography operation as described above was repeated for the obtained GT fractions to further purify the GT.

In 1.0 ml of phosphate buffered saline (PBS), 0.5 mg of the thus obtained cancer-related GT was dissolved and this solution was used as the immunogen.

Immunization and Cell Fusion

To a Balb/c mouse (female, 6 weeks old), 0.2 ml of a uniform mixture of 0.5 ml of the immunogen described above and 0.5 ml of Freund's complete adjuvant was intraperitoneally administered. Three weeks after the first immunization, 0.2 ml of the same mixture as used in the first immunization except that Freund's incomplete adjuvant was used in place of the Freund's complete adjuvant was intraperitoneally administered. Two weeks after the second immunization, 100 μg of the immunogen alone was injected in a tail vein.

Three days after the final immunization, spleen cells of the mouse were taken and washed with RPMI 1640 medium. A cell suspension containing $4 \times 10^8$ spleen cells and a cell suspension containing $8 \times 10^7$ mouse myeloma cells (X63-Ag8.653) were mixed and the medium was removed by centrifugation. In a water bath at 37° C., 1 ml of polyethylene glycol-RPMI 1640 medium was gradually added and the cell mixture was gently stirred so as to allow cell fusion. The medium was then removed by centrifugation and 40 ml of RPMI 1640 medium containing 15% by weight of fetal calf serum (FCS) was added. The resulting mixture was placed in the wells of a 96-well microplate in the amount of 0.15 ml/well. On the next day, 0.15 ml of HAT medium (RPMI 1640 medium containing $4 \times 10^{-7}$M aminoputerin, $1.6 \times 10^{-5}$M thymidine, $1 \times 10^{-4}$M hypoxanthine and 10% by weight of FCS) was added to the each well. Half volume of the medium in each well was replaced with fresh HAT medium every 3 or 4 days. After 2 weeks from the beginning of the culture, the growth of hybridomas was observed in 80% of the wells.

Selection of Hybridomas

The screening of the monoclonal antibody contained in the supernatant of the hybridoma culture medium was carried out by ELISA using the cancer-related GT obtained above as an antigen.

More particularly, 2 μg/ml of the antigen in PBS was adsorbed to wells in a microtiter plate for ELISA and the wells were blocked with 1% BSA in PBS. The culture media of the hybridomas were separately placed in the wells in the microtiter plate for ELISA so as to allow antibody-antigen reaction. Goat anti-mouse immunoglobulin antibody labelled with peroxidase was then reacted with the reaction product and o-phenylenediamine which is a substrate of peroxidase was added to the wells, followed by measurement of absorbance at 492 nm. As a result, 8 hybridomas which react with the cancer-related GT and which do not react with serum proteins were obtained in 14 times run of the cell fusion process.

The thus obtained hybridomas were transferred to HT medium (HAT medium from which aminoputerin is removed), and then transferred to RPMI 1640 medium containing 10% by weight of FCS.

The thus obtained hybridomas were then cloned by the limiting dilution method. That is, cell suspensions of the hybridomas were placed in wells of a microplate after sufficient dilution so as to attain a cell population of 0.5-4 cells per well. The hybridomas were cultured with $1 \times 10^6$/well of mouse thymus cells. After two weeks from the beginning of this culture, the hybridomas producing the desired monoclonal antibody were selected by the above-described ELISA.

The above-described operation was repeated to obtain stable hybridomas MAb7907, MAb8513, MAb8677, MAb8628, MAb8507, MAb8611, MAb8913 and MAb8919 were established.

By the conventional ELISA, the class of the thus obtained monoclonal antibodies was determined. As a result, monoclonal antibodies MAb7907 and MAb8513 were classified as IgM, MAb8628, MAb8677, MAb8507, MAb8611 and 1 MAb8919 were classified as IgG$_1$, MAb8913 was classified as IgG$_2$b. Hybridomas MAb7907, MAb8513, MAb8628 and MAb8677 were deposited with Fermentation Research Institute of Japan under the Budapest Treaty under accession numbers of FERM BP-3279, FERM BP-3278, FERM BP-3280 and FERM BP-3281, respectively.

EXAMPLE 8

Analysis of Epitope of Antigen

The purified antigen obtained in Example 7 was dissolved in PBS to a concentration of 1 μg/ml and the resulting solution was adsorbed in the wells of a microtiter plate. The wells were washed with PBS and blocked with 1% by weight of BSA. Monoclonal antibodies MAb4880 and MAb7907 were labelled with horse radish peroxidase (HRP) by the conventional periodic acid method (The monoclonal antibodies labelled with HRP are hereinafter expressed as MAb4880-HRP, MAb7907-HRP or the like. Further, the monoclonal antibodies labelled with HRP are collectively referred to as "labelled body"), and the thus obtained labelled bodies were 2000-fold diluted with 1 wt% BSA solution. To each well, 100 μl of the resulting labelled body solution was added and the reaction was allowed to occur at 37° C. for 1 hour. After the reaction, the wells were washed with PBS and o-phenylenediamine was added to the wells, followed by the measurement of the absorbance at 492 nm of the solution in each well. On the other hand, to MAb4880-HRP or MAb7907-HRP, the monoclonal antibodies shown in Table 3 were added to a final concentration of 10 μg/ml and the same operation as described above was repeated so as to observe the influence by the addition of the monoclonal antibodies. The measured absorbance is shown in Table 3.

TABLE 3

| MAb Admixed with Labelled Body | Labelled Body MAb4880-HRP | Labelled Body MAb7907-HRP |
|---|---|---|
| 4880 | 0.709 | >2.000 |
| 7907 | >2.000 | 0.192 |
| 8507 | 0.235 | >2.000 |
| 8513 | >2.000 | 0.013 |
| 8611 | >2.000 | >2.000 |
| 8628 | 0.059 | >2.000 |
| 8677 | >2.000 | 0.112 |
| 8913 | >2.000 | >2.000 |
| 8919 | >2.000 | >2.000 |
| 1% BSA | >2.000 | >2.000 |

From the results shown in Table 3, the monoclonal antibodies may be classified into three groups as follows:

Group 1: MAb4880, MAb8507 and MAb8628
Group 2: MAb7907, MAb8513 and MAb8677
Group 3: MAb8611, MAb8913 and MAb8919

It is expected that when a sandwich assay is carried out, combinations of the monoclonal antibodies belonging to the same group should be avoided. Further, as described in Example 9 below, the monoclonal antibodies of the present invention are those belonging to Group 2. When carrying out a sandwich assay, it is preferred to fix the monoclonal antibody of the present invention belonging to Group 2 to a solid carrier and to use the monoclonal antibody belonging to Group 1 as the second antibody.

EXAMPLE 9

Biotin was attached to the antigen obtained in Example 7 and was fractioned by gel permeation chromatography Sup-12 FPLC (commercially available from Pharmacia) (solvent: PBS; flow rate: 0.5 ml/min). The fraction of the molecular weight of from about 500,000 to about 2,000,000 was named P-1, and the fraction of the molecular weight of about 50,000 to about 300,000 was named P-2. The various monoclonal antibodies at a concentration of 10 μg/ml shown in Table 4 were fixed to the wells in a microtiter plate. After blocking the wells with 1% BSA, P-1 or P-2 diluted with 1 wt% of BSA to a prescribed concentration was added to each well in the amount of 100 μl/well and the reaction was allowed to occur at 37° C. for 1 hour. After the reaction, the wells were washed with PBS and streptoavidin-HRP 2000-fold diluted with 1 wt% BSA was added to each well in the amount of 100 μl/well. The reaction was allowed to occur at room temperature for 30 minutes. After the reaction, the wells were washed with PBS and o-phenylenediamine was added to the wells, followed by the measurement of absorbance at 492 nm. The results are shown in Table 4.

TABLE 4

| Immobilized MAb | P-1 | | | P-2 | | |
|---|---|---|---|---|---|---|
| | 1:100 | 1:300 | 1:900 | 1:100 | 1:300 | 1:900 |
| 4880 | >2.000 | 0.615 | 0.207 | 0.451 | 0.171 | 0.062 |
| 7907 | 0.751 | 0.380 | 0.144 | 0.066 | 0.034 | 0.015 |
| 8507 | 1.860 | 0.603 | 0.193 | 0.366 | 0.160 | 0.052 |
| 8513 | 0.687 | 0.227 | 0.079 | 0.063 | 0.033 | 0.019 |
| 8611 | 0.100 | 0.028 | 0.013 | 0.839 | 0.309 | 0.100 |
| 8628 | >2.000 | 0.625 | 0.178 | 0.851 | 0.346 | 0.121 |
| 8677 | 0.295 | 0.096 | 0.019 | 0.024 | 0.016 | 0.014 |
| 8913 | 1.207 | 0.400 | 0.082 | 0.527 | 0.241 | 0.098 |
| 8919 | 0.126 | 0.066 | 0.023 | 0.827 | 0.454 | 0.226 |
| Control | 0.020 | 0.016 | 0.013 | 0.039 | 0.020 | 0.012 |

EXAMPLE 10

Plastic beads with a diameter of ¼ inch were treated with a solution of the monoclonal antibody MAb8513 of the present invention with a concentration of 10 μg/ml at 4° C. overnight so as to fix the antibody to the plastic beads. After washing the beads with PBS, the beads were blocked with 1% BSA solution in PBS at 37° C. for 24 hours. To a reaction tray, 50 μl of a serum sample, 150 μl of 100 mM phosphate buffer (pH 6.0) containing 1M NaCl and the beads treated as above were added so as to allow the reaction at 45° C. for 2 hours. The samples tested were collected from 27 patients suffering from ovarian cancer, 53 patients suffering from benign ovarian tumor and 37 normal persons. After the reaction, the beads were washed three times with PBS and 200 μl of MAb8628-HRP diluted 2000-fold with 20 mM phosphate buffer (pH 7.3) containing 1 wt% BSA and 1M NaCl was added so as to allow the reaction at 37° C. for 1 hour. After the reaction, the beads were washed 4 times with PBS and were transferred to a test tube containing 300 μl of o-phenylenediamine solution with a concentration of 3 mg/ml. The coloring reaction was allowed to occur at room temperature for 30 minutes. After the reaction, 1 ml of 1N sulfuric acid was added to the test tube and the absorbance was measured at 492 nm. The enzyme activity was measured based on a preliminarily prepared calibration curve. The results are shown in FIG. 4.

Figure 4:
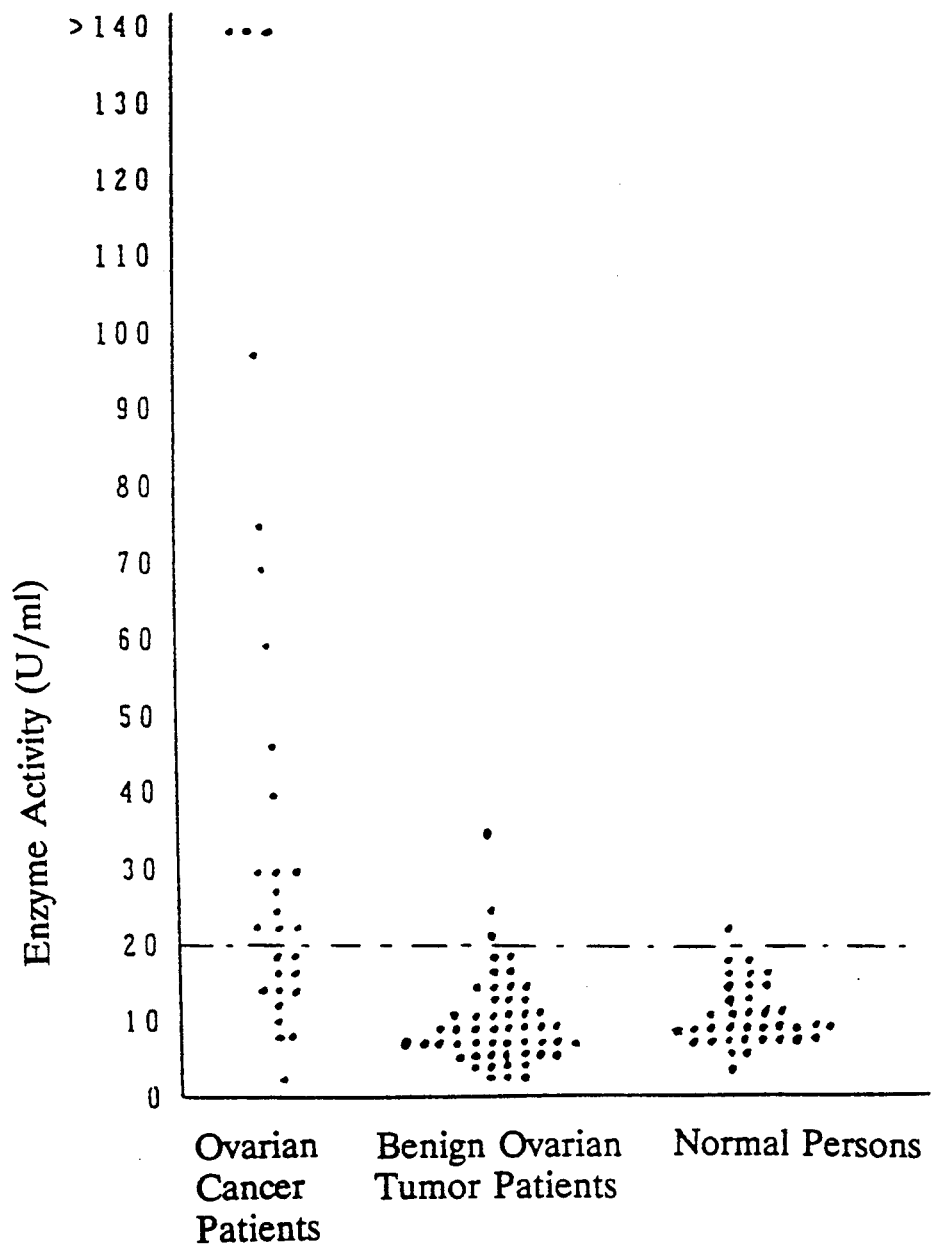
FIG. 4 shows the results of the measurements of the cancer-related human galactosyltransferase in sera from ovarian cancer patients, benign ovarian tumor patients and from normal persons.

As can be seen from FIG. 4, it was confirmed that diagnosis of ovarian cancer can be carried out by using the monoclonal antibody of the present invention.

We claim:

1. Essentially pure cancer-related human galactosyltransferase which has a molecular weight of about 50,000 as determined by SDS-polyacrylamide gel electrophoresis after treatment with 10 mM 2-mercaptoethanol, which has a reactivity with MAb4880 (FRI BP-1758) and has no reactivity with MAb3872 (ATCC HB8945) under native conditions, a part of the galactosyltransferase self-associates, the reactivity with MAb4880 and the degree of self-association are promoted by treatment with 10 mM 2-mercaptoethanol at 80° C. for three minutes so that a part of the galactosyltransferase is detected in a fraction of a molecular weight of not less than 200,000 to 1,000,000 by gel permeation chromatography.

2. The human galactosyltransferase of claim 1, which is obtained from ascites of a cancer patient by α-lactoalbumin agarose affinity chromatography.

3. The human galactosyltransferase of claim 1, wherein a part of the galactosyltransferase is detected in a fraction of a molecular weight of not less than 200,000 to 500,000 by gel permeation chromatography.

4. The human galactosyltransferase of claim 2, wherein the ascites are from a cancer patient suffering from ovary cancer.

5. The human galactosyltransferase of claim 1, wherein the optimal pH range and the stable pH range of the galactosyltransferase is 6 to 8.

* * * * *